United States Patent
Hsu

(10) Patent No.: US 8,771,485 B2
(45) Date of Patent: Jul. 8, 2014

(54) TEST STRIP

(75) Inventor: Tien-Tsai Hsu, Hsinchu County (TW)

(73) Assignee: HMD Biomedical Inc., Hsinchu County (TW)

( * ) Notice: Subject to any disclaimer, the term of this patent is extended or adjusted under 35 U.S.C. 154(b) by 124 days.

(21) Appl. No.: 13/360,946

(22) Filed: Jan. 30, 2012

(65) Prior Publication Data

US 2012/0193228 A1    Aug. 2, 2012

(30) Foreign Application Priority Data

Jan. 31, 2011    (TW) .............................. 100103788 A

(51) Int. Cl.
*G01N 27/26*    (2006.01)
*A61B 5/00*    (2006.01)

(52) U.S. Cl.
USPC ..... 204/403.01; 600/583; 600/347; 422/68.1; 422/82.01; 435/287.1

(58) Field of Classification Search
USPC ........ 204/403.01–403.15; 600/380–583, 347; 205/792, 775, 778; 422/68.1, 82.01; 435/287.1
See application file for complete search history.

(56) References Cited

U.S. PATENT DOCUMENTS

| | | | |
|---|---|---|---|
| 4,790,979 A | 12/1988 | Terminiello et al. | |
| 5,563,042 A | 10/1996 | Phillips et al. | |
| 6,071,251 A | 6/2000 | Cunningham et al. | |
| 6,506,168 B1 | 1/2003 | Fathallah et al. | |
| 7,192,405 B2 * | 3/2007 | DeNuzzio et al. | ............ 600/583 |
| 7,640,047 B2 | 12/2009 | Sakata et al. | |
| 7,785,271 B2 | 8/2010 | Fujiwara et al. | |
| 2004/0171968 A1 | 9/2004 | Katsuki et al. | |
| 2005/0011759 A1 * | 1/2005 | Moerman et al. | ........ 204/403.03 |
| 2005/0123443 A1 * | 6/2005 | Fujiwara et al. | ................. 422/58 |
| 2006/0184189 A1 * | 8/2006 | Olson et al. | .................... 606/181 |
| 2009/0214384 A1 * | 8/2009 | Wang et al. | ..................... 422/56 |
| 2011/0015545 A1 * | 1/2011 | Mondro | ........................ 600/583 |

FOREIGN PATENT DOCUMENTS

| | | |
|---|---|---|
| CN | 1554019 A | 12/2004 |
| CN | 101241141 A | 8/2008 |
| CN | 101351153 A | 1/2009 |
| JP | 2001-289816 A | 10/2001 |
| WO | WO93/03673 | 3/1993 |

* cited by examiner

*Primary Examiner* — Jennifer Dieterle
(74) *Attorney, Agent, or Firm* — Rosenberg, Klein & Lee

(57) ABSTRACT

A test strip is revealed. The test strip includes a detection area, at least one outer sampling area, and a circuit system. The detection area includes a sampling hole, at least one sampling channel corresponding to the sampling hole, and at least one reaction area in the sampling channel. An inner sampling area is disposed around the sampling hole and an inner sampling opening is on an edge of the inner sampling area for communicating with the sampling channel and the sampling hole. The outer sampling area is located on an outer side of the test strip. The outer sampling area includes an outer sampling opening in communication with the sampling channel. The circuit system is electrically connected to the reaction area. The test strip further includes at least one pressing part located around the sampling hole for pressing against a test area and preventing cross-infection.

14 Claims, 18 Drawing Sheets

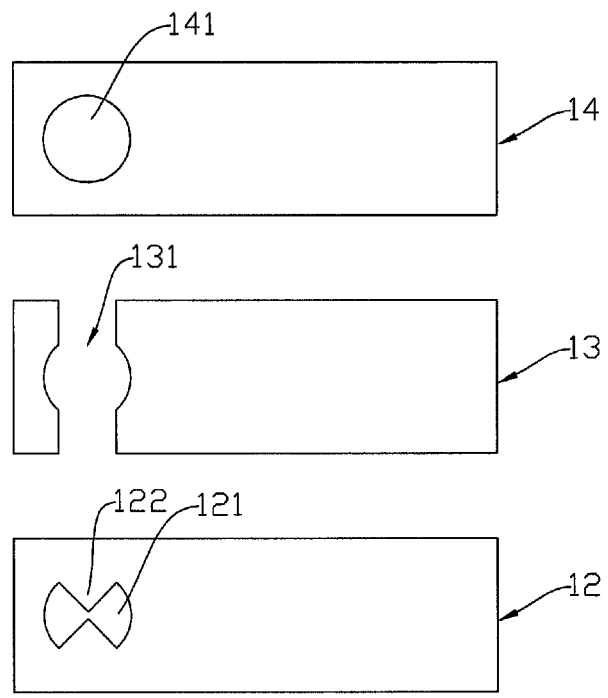
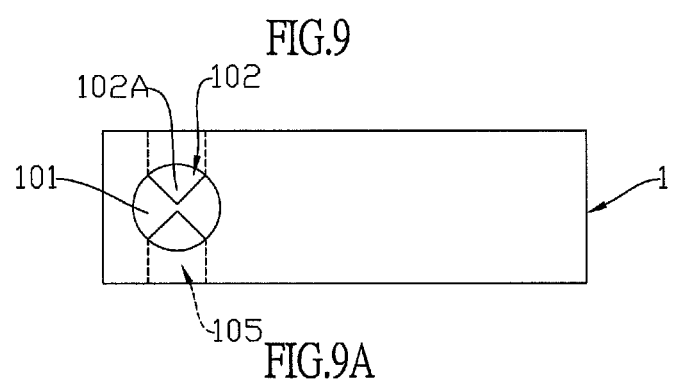
FIG.9
FIG.9A

TEST STRIP

BACKGROUND OF THE INVENTION

1. Field of the Invention

The present invention relates to a test strip, especially to a test strip with sample collection and guiding effect. The test strip is used in conjunction with a test device having sampling and testing functions.

2. Descriptions of Related Art

In early days, most of test items are run at specific places such as hospitals, or laboratory medicine offices, laboratories by medical instruments and medical staffs. Along with fast development of biological testing technology, now patients can do some tests by themselves at home without being monitored by medical staffs.

For example, many diabetes patients need to test blood glucose levels at least one time per day. There are several systems available now for patients to monitor their blood glucose levels conveniently. The system generally includes a test strip for users to collect the blood sample, and a test meter used to read the blood glucose level.

Nowadays electrochemical technology is widely used for determining the concentration of glucose in the blood. A test strip usually includes a reaction area with specific enzyme reagents (such as Glucose oxidase (GOx) and medium). When a user gets a blood sample into the reaction area, the test meter applies a voltage to the test strip. The specific enzyme reagents react with glucose in the blood sample and electrochemical reaction occurs. Then the test meter measures an electric current generated and calculates the blood glucose level according to the electric current.

Blood sample collection and blood sample testing are performed by using different devices. The blood sample collection is by using a lancing device having a lancet together with a test strip. The blood sample testing is run by using the test meter mentioned above. Firstly the user uses the lancing device to prick skin on a test area and squeeze the test area to draw blood drops to the reaction area of the test strip. Then the test strip is inserted into the test meter for measurement. The lancing device may be used repeatedly. Blood contamination is present on the contact area between the lancing device and the user. This leads to cross-infection between users.

There is a test device that combines the lancing device and the test meter available now. Yet the structure of this kind of test device is quite complicated. Moreover, the test device is difficult to use and maintain. For example, a method and apparatus for obtaining samples of blood for diagnostic purposes are revealed in the U.S. Pat. No. 6,506,168. The apparatus includes a movable support for supporting and positioning a port for a fluid collector in a sealable chamber. The movable support is capable of moving the port within the sealable chamber between different positions. The apparatus further includes a vacuum pump in communication with the sealable chamber for enhancing collection of blood samples from an opening in the skin. Besides the above two parts, the apparatus still has other parts. Due to the complicated structure, the apparatus tends to be out of order quite often. Thus it is not the ideal design.

In order to solve the above problems, there is a need to provide a test strip with novel design that collects samples easily. When the test strip is applied together with a test device with sampling and testing functions, the structure of the test device is not complicated and there is no cross-infection occurred.

SUMMARY OF THE INVENTION

Therefore it is a primary object of the present invention to provide a test strip that performs tests by electrochemical reactions. An inner sampling area disposed around a sampling hole of the test strip is used to collect samples and guide samples entering to at least one reaction area where electrochemical reactions occur.

It is another object of the present invention to provide a test strip that prevents cross-infection by at least one pressing part located around a sampling hole. The pressing part is used to press against a test area of a person to be tested, allowing samples flowing from the test area to at least one reaction area where electrochemical reactions occur. The test strip is used together with a test device having sampling and testing functions.

In order to achieve the above objects, a test strip of the present invention comprises a detection area, at least one outer sampling area and a circuit system. The detection area includes a sampling hole, at least one sampling channel corresponding to the sampling hole, at least one reaction area located in the sampling channel and an inner sampling area disposed around the sampling hole and having an inner sampling opening on an edge thereof for communicating the sampling channel and the sampling hole. The outer sampling area is located on an outer side of the test strip and having an outer sampling opening that communicates with the sampling channel. The circuit system is electrically connected to the reaction area.

Besides the sampling hole, the sampling channel corresponding to the sampling hole and the reaction area located in the sampling channel, the detection area further includes at least one pressing part located around the sampling hole.

The present invention features on that the test strip is capable of collecting samples easily and is used together with a test device with sampling and testing functions so as to prevent cross-infection.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein:

FIG. 9 and FIG. 9A are schematic drawings showing a further mode of a test trip with multiple layers according to the present invention;

DETAILED DESCRIPTION OF THE PREFERRED EMBODIMENT

Figure 1:
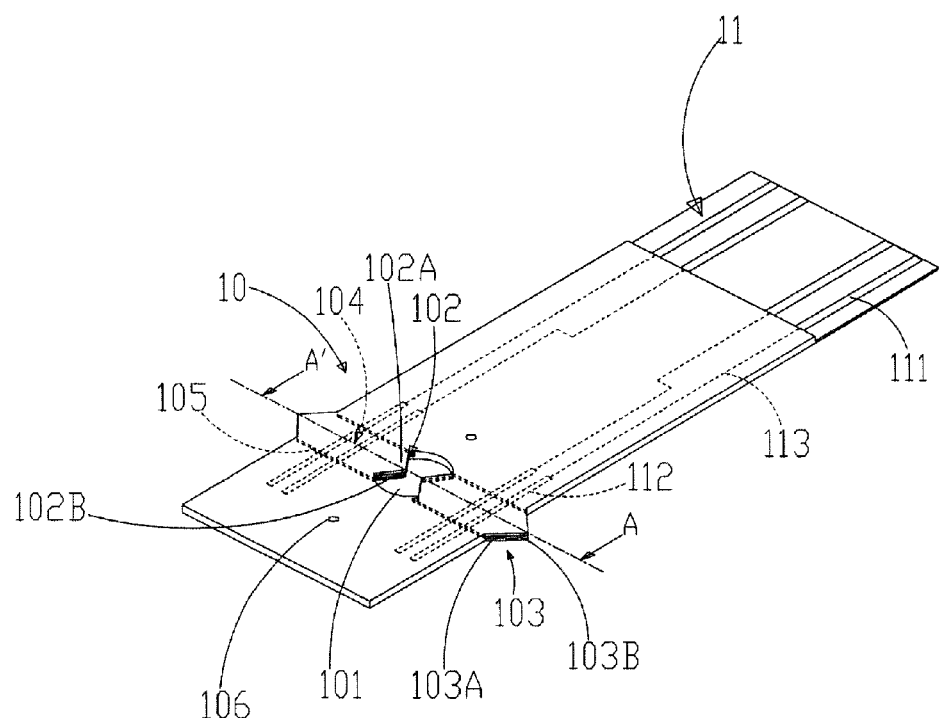
FIG. 1 is a perspective view of an embodiment according to the present invention.
Figure 2:
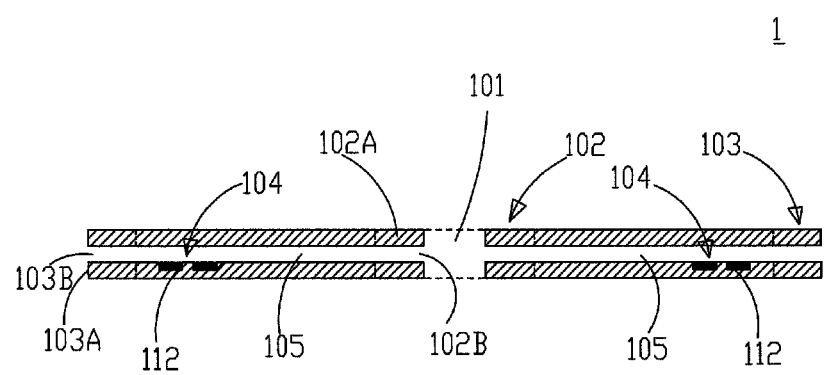
FIG. 2 is a cross sectional view along AA' line of the embodiment in FIG. 1.

Refer to FIG. 1 and FIG. 2, a test strip 1 of the present invention used for tests is based on electrochemical techniques. The test strip 1 mainly includes a detection area 10 and a circuit system 11. The detection area 10 is for collecting a sample 4 (such as blood) and running related tests. The detection area 10 includes a sampling hole 101, two reaction areas 104 and two sampling channels 105. The sampling hole 101 is an insertion hole, allowing a blood lancet 23 passing through and collected a blood sample 4 from a person to be tested. Each reaction area 104 is located in the two sampling channels 105 respectively. An inner sampling area 102 is disposed around the sampling hole 101. The inner sampling area 102 is composed of two inner sampling projections 102A and two inner sampling openings 102B. The inner sampling projection 102A extends from an edge of the sampling channel 105 to the position near a center of the sampling hole 101. The inner sampling opening 102B is on one edge of the inner sampling projection 102A corresponding to the sampling hole 101 and is communicated with the sampling channel 105. Thus the sampling channel 105 extends near the center of the sampling hole 101 for convenience of collecting blood. In other words, the inner sampling projection 102A is located between the sampling hole 101 and the sampling channel 105. The inner sampling opening 102B and the reaction area 104 are connected to each other by the sampling channel 105. The sample 4 collected from the sampling hole 101 enters the inner sampling opening 102B, passes through the sampling channel 105 and arrives each of the reaction areas 104. Thus two sets of test signals are generated by electrochemical reactions of the sample 4 occurring in the reaction rear 104.

Figure 3:
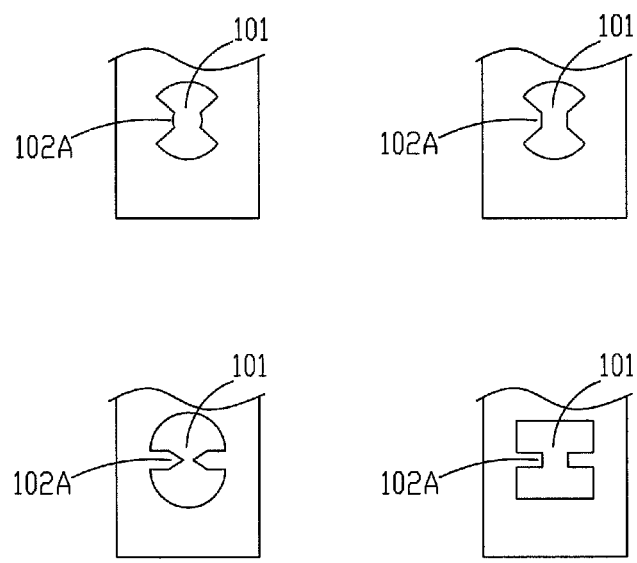
FIG. 3 shows schematic drawings showing various types of a sampling hole according to the present invention.
Figure 4:
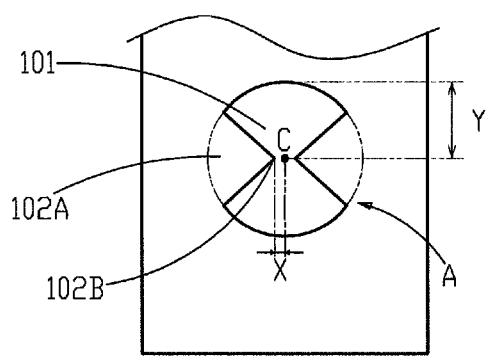
FIG. 4 is an enlarged view of a sampling hole according to the present invention.

Refer to FIG. 3, the sampling hole 101 can be in various types as shown in the figure. As shown in the FIG. 4, the sampling hole 101 of the test strip 1 is a round hole A (or of other shapes such as polygonal shape, oval shape, etc.). The inner sampling projection 102A projects into the round hole A from one edge thereof, located inside the round hole A. The rest part of the round hole A is the sampling hole 101. The distance between the inner sampling opening 102B of the inner sampling projection 102A and the center of the sampling hole 101 is represented by X. The distance X is smaller than a radius Y of the round hole A. This means the inner sampling opening 102B on the front end of the inner sampling projection 102A is getting closer to the center C of the sampling hole 101 than most of other positions of the sampling hole 101 (round hole A). Thus the inner sampling opening 102B have better blood drawing and guiding effect. The preferred distance X ranges from 0.2 mm to 2 mm.

In other embodiments, the test strip 1 further includes an outer sampling area 103 outside the detection area 10. The outer sampling area 103 consists of an outer sampling projection 103A and an outer sampling opening 103B. The outer sampling opening 103B is located on one edge of the outer sampling projection 103A and communicated with the sampling channel 105. The outer sampling projection 103A is another area for sample collection, allowing blood passing through the outer sampling opening 103B and the sampling channel 105 to the reaction area 104. The outer sampling projection 103A can collect samples independently and then the test is performed. Moreover, the outer sampling opening 103B can be used as an air vent of the sampling channel 105, corresponding to the inner sampling opening 102E on the other end of the sampling channel 105 for convenient blood drawing and guiding. Furthermore, the test strip 1 is disposed with at least one positioning part 106 around the sampling hole 101. The positioning part 106 can be an insertion hole, a notch or a bump used for positioning the test strip 1 on corresponding test device 2.

The circuit system 11 consists of two sets of circuit connection part 111 and two sets of test electrode 112. The circuit connection part 111 is located on one end of the test strip 1, opposite to the end with the detection area 10 and is electrically connected to test device 2 for sending test signals to the test device 2 and performing analysis. The test electrode 112 is located on the reaction area 104 so that test signals are transmitted from the reaction area 104 to the test device 2 by the test electrode 112. The test electrode 112 includes at least one working electrode and one reference electrode. The test electrodes 112 are connected to the circuit connection parts 111 by wires 113 respectively. The number of the inner sampling opening 102B, the reaction area 104, the sampling channel 105 and the test electrode 112 mentioned above can be two (or two sets) but is not limited.

Figure 5:
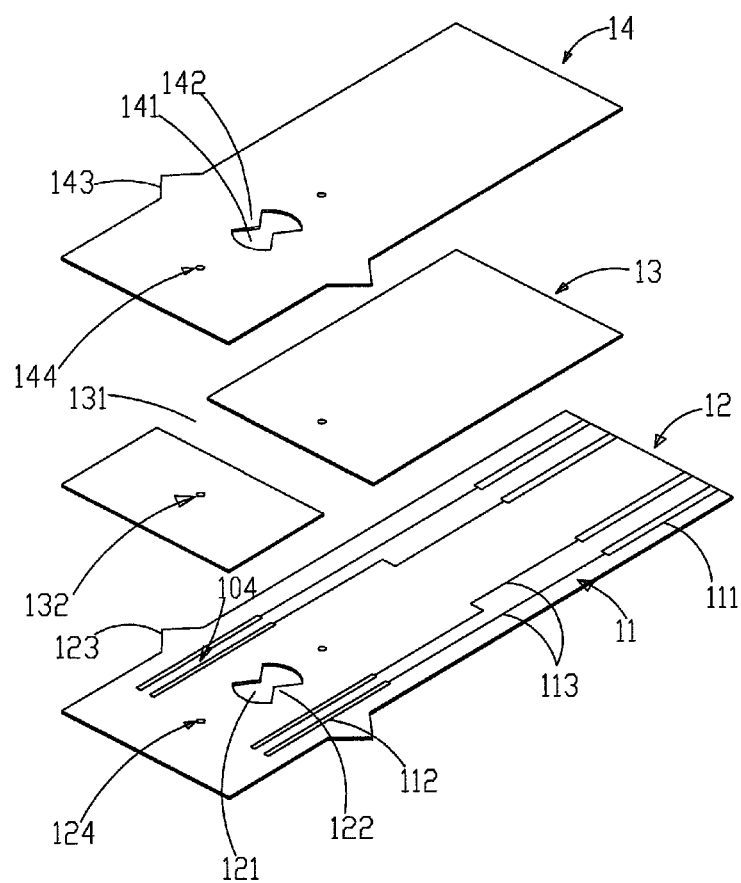
FIG. 5 is an explosive view of the embodiment in FIG. 1.

Refer to FIG. 5, an explosive view of an embodiment according to the present invention is revealed. The test strip 1 includes a substrate 12, a spacer layer 13 and an upper cover 14. A substrate hole 121 is located on the substrate 12 corresponding to the detection area 10 of the test strip 1. There are two reaction areas 104 around the substrate hole 121. Two substrate inner projections 122 are respectively disposed on two sides of the substrate hole 121 and corresponding to the reaction areas 104. Each substrate inner projection 122 is formed by an edge of the substrate hole 121 extends and projects toward a center of the substrate hole 121. Moreover, the substrate 12 is disposed with circuit connection parts 111, test electrodes 112, and wires 113. A substrate outer projection 123 is located on each of two sides of the substrate 12.

The spacer layer 13 is above the substrate 12. The detection area 10 and the circuit connection parts 111 of the test strip 1 are exposed, not being covered by the spacer layer 13. The spacer layer 13 includes a channel gap 131 that is corresponding to the substrate hole 121 and the substrate inner projections 122 of the substrate 12. While the spacer layer 13 is covered over the substrate 12, the channel gap 131 forms the detection area 10 of the test strip 1 (between the substrate 12 and the upper cover 14).

The upper cover 14 is covered over the spacer layer 13. The upper cover 14 includes an upper cover hole 141 corresponding to the substrate hole 121. The upper cover hole 141 is arranged with upper-cover inner projections 142 on two sides thereof and the upper-cover inner projections 142 are corresponding to the substrate inner projections 122. An upper-cover outer projection 143 is disposed on each of two sides of the upper cover 14. The upper-cover outer projection 143 is corresponding to and assembled with the substrate outer projection 123 so as to form the outer sampling projection 103A and the outer sampling opening 103E therebetween.

The substrate 12, the spacer layer 13 and the upper cover 14 are stacked to form the test strip 1. An overlapped area of the substrate hole 121, the channel gap 131 and the upper cover hole 141 is defined as the sampling hole 101 of the test strip 1. Due to the channel gap 131, an inner sampling area 102 is formed between the substrate inner projections 122 and the upper-cover inner projections 142 and the sampling channels 105 on each of the two sides of the sampling hole 101 are formed between the substrate 12 and the upper cover 14. The sampling channel 105 communicates the inner sampling area 102, the sampling hole 101 and the two reaction areas 104. Moreover, if the positioning part 106 is an insertion hole, the substrate 12, the spacer layer 13 and the upper cover 14 are respectively disposed with a corresponding substrate positioning part 124, a spacer layer positioning part 132 and an upper cover positioning part 144 that are all insertion holes. When the positioning part 106 is a cut (notch), the cut is set on a side of the substrate 12, the spacer layer 13 and the upper cover 14 (not shown in figure). When the positioning part 106 is a bump, the bump is mounted on the substrate 12 or the upper cover 14 (not shown in figure).

While collecting blood by using the sampling hole 101, the sample 4 (blood) can contact the inner sampling opening 102B quickly because the inner sampling area 102 is close to the sampling hole 101. By the capillary action, the blood passes through the sampling channels 105 to the two reaction areas 104. Thus an electrical signal is generated from the reaction area 104, and then is sent through the test electrode 112, the wire 113 and then to the circuit connection part 111.

Figure 6:
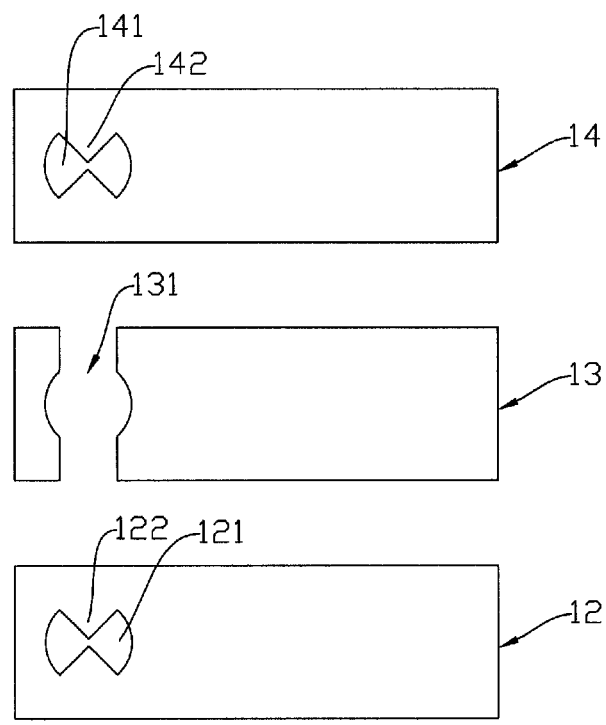
FIG. 6 and FIG. 6A are schematic drawings showing a mode of a test trip with multiple layers according to the present invention.
Figure 6A:
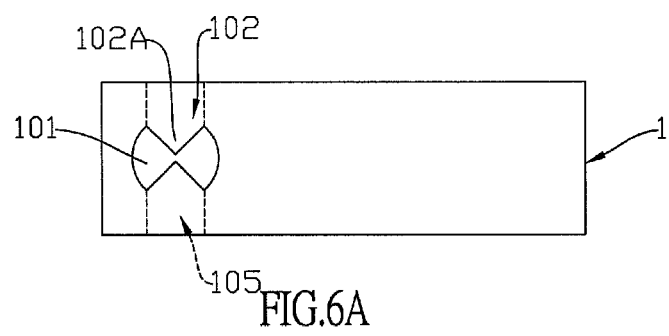

Refer from FIG. 6 to FIG. 11, a plurality of embodiments with different combinations of the layers of the test strip 1 are revealed. As shown in FIG. 6 and FIG. 6A, the upper cover 14 is disposed with the upper cover hole 141 and the upper-cover inner projections 142 while the substrate 12 is arranged with the substrate hole 121 and the substrate inner projections 122. The upper-cover inner projections 142 and the substrate inner projections 122 are with the same size, symmetrical to and assembled with each other so as to form the inner sampling area 102.

Figure 7:
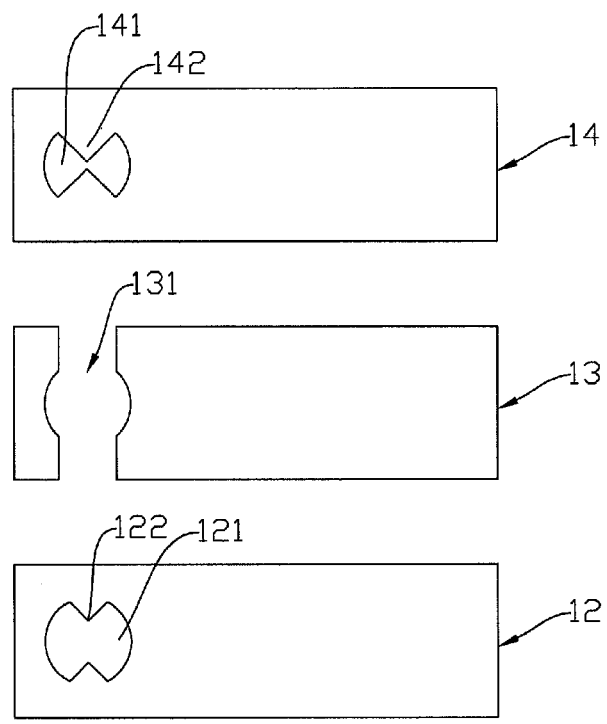
FIG. 7 and FIG. 7A are schematic drawings showing another mode of a test trip with multiple layers according to the present invention.
Figure 7A:
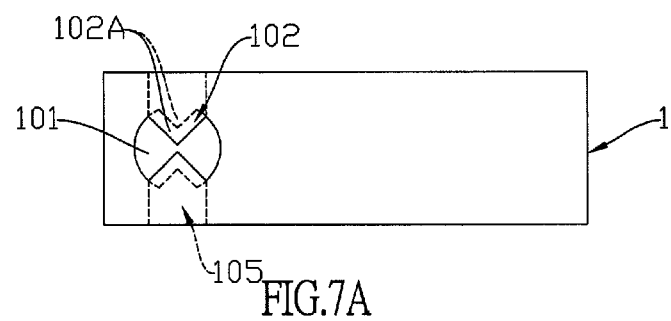
Figure 8:
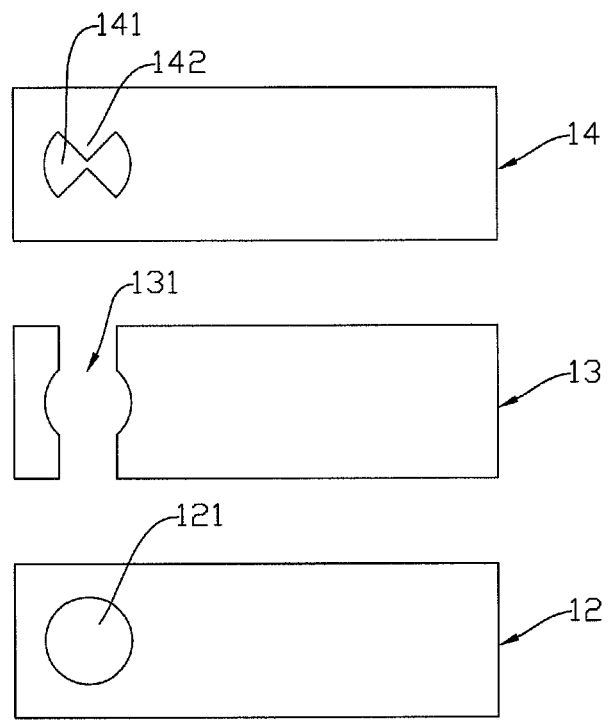
FIG. 8 and FIG. 8A are schematic drawings showing a further mode of a test trip with multiple layers according to the present invention.
Figure 8A:
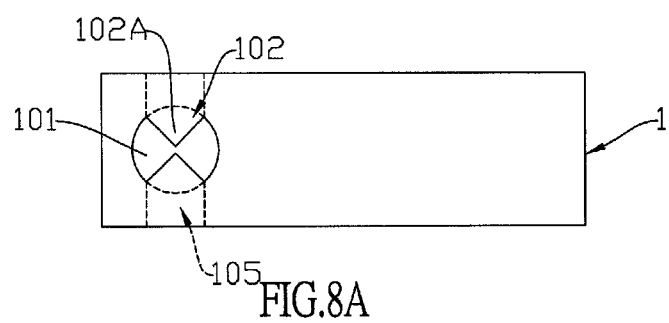
Figure 10:
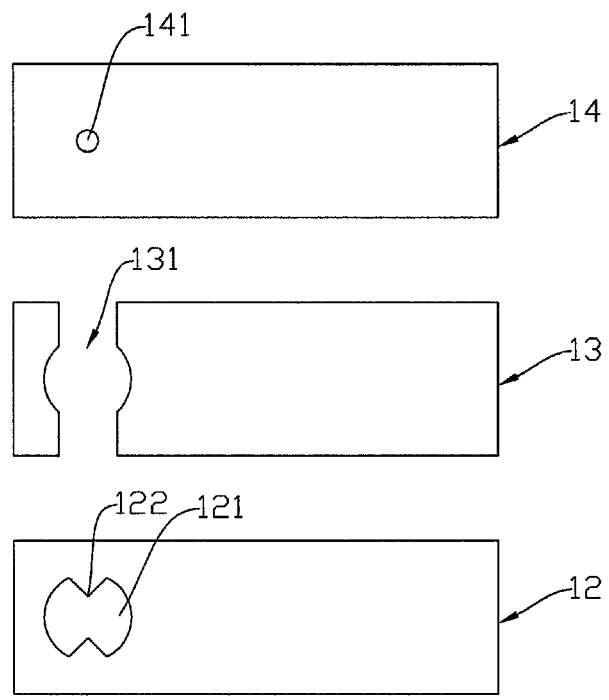
FIG. 10 and FIG. 10A are schematic drawings showing a further mode of a test trip with multiple layers according to the present invention.
Figure 10A:
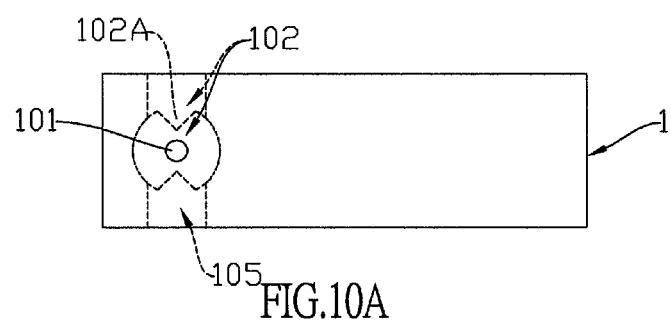

Refer to FIG. 7 and FIG. 7A, the upper-cover inner projections 142 and the substrate inner projections 122 are with different size and are assembled with each other to form the inner sampling area 102. Refer to FIG. 8 and FIG. 8A the substrate hole 121 of the substrate 12 is a round hole without the substrate inner projections 122. The inner sampling area 102 is formed only by the upper-cover inner projections 142 of the upper cover 14. Refer to FIG. 9 and FIG. 9A, the upper cover hole 141 of the upper cover 14 is a round hole without upper-cover inner projections 142. The inner sampling area 102 is formed only by the inner projections 122 of the substrate 12. Refer to FIG. 10 and FIG. 10A, the upper cover hole 141 of the upper cover 14 is a small round hole without the upper-cover inner projections 142. The area among the substrate inner projections 122 of the substrate 12, the upper cover hole 141 and the substrate hole 121 forms the inner sampling area 102.

Figure 11:
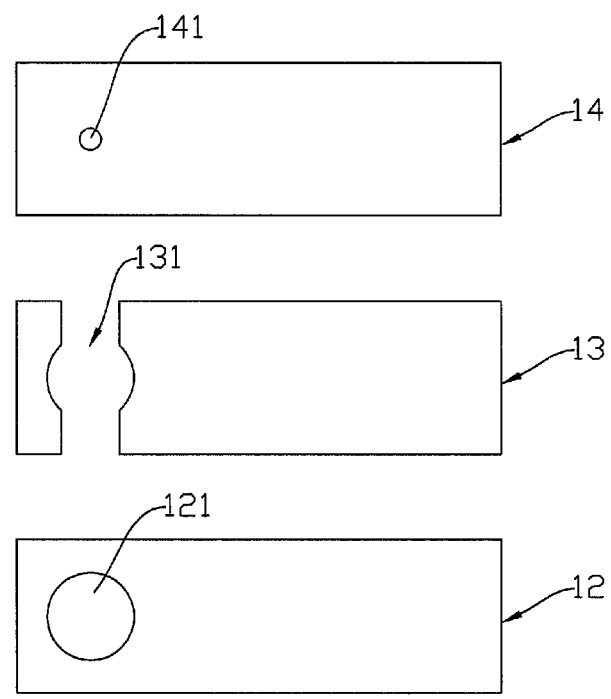
FIG. 11 and FIG. 11A are schematic drawings showing a further mode of a test trip with multiple layers according to the present invention.
Figure 11A:
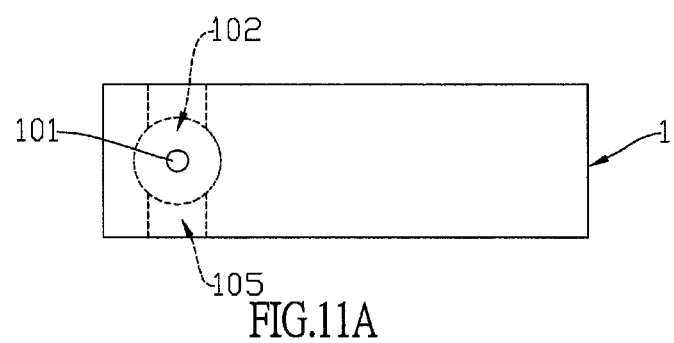

Refer to FIG. 11 and FIG. 11A, the upper cover hole 141 of the upper cover 14 is a small round hole without the upper-cover inner projections 142 while the substrate hole 121 of the substrate 12 is a larger round hole without the substrate inner projections 122. The upper cover hole 141 and the substrate hole 121 are different diameters. The area between the upper cover hole 141 and the substrate hole 121 forms the inner sampling area 102. In the above embodiments, the inner sampling projection 102A is composed of one of the substrate inner projections 122 of the substrate 12 or/and one of the upper-cover inner projections 142 of the upper cover 14. The inner sampling area 102 is formed by the inner sampling projections 102A, an area between the substrate hole 121 and the upper cover hole 141 having different diameters respectively or their combinations. The sampling hole 101 is formed by overlapped area of the substrate hole 121 and the upper cover hole 141. The diameter of the sampling hole 101 ranges from 0.4 mm to 4 mm.

Figure 12:
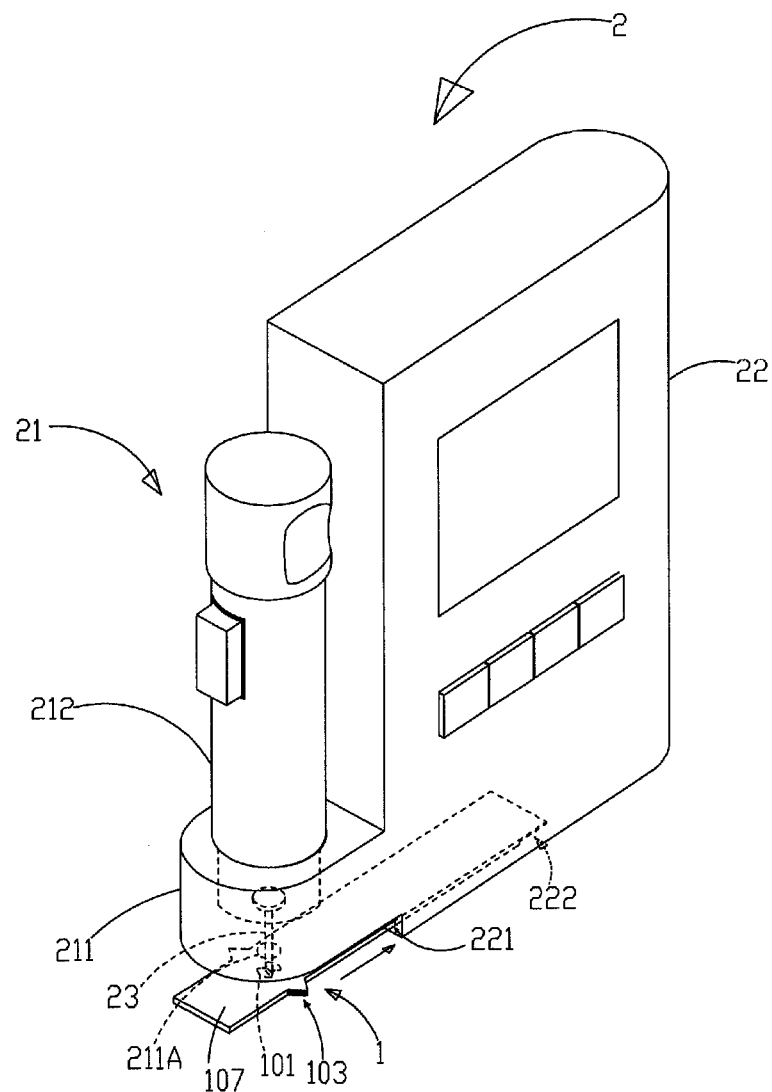
FIG. 12 is a schematic drawing showing an embodiment of a test strip in use according to the present invention.
Figure 13:
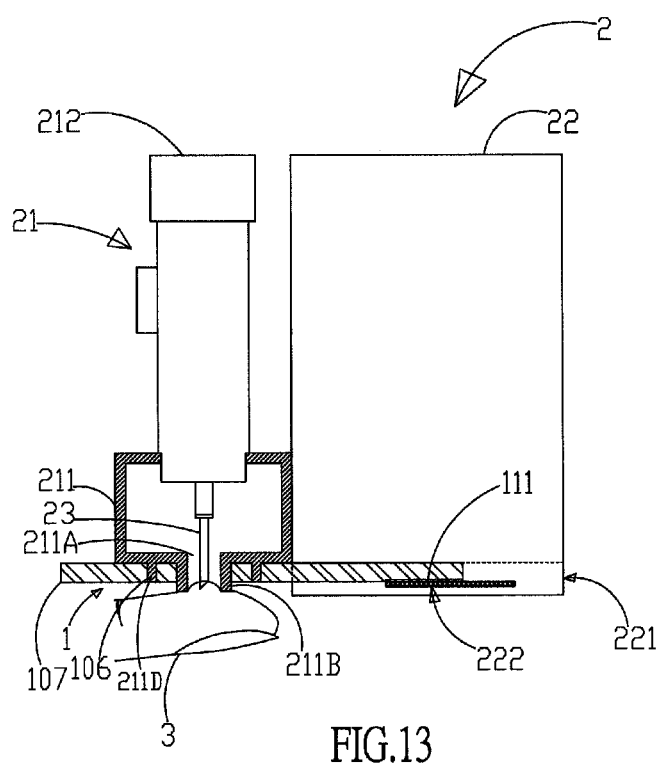
FIG. 13 is a partial cross sectional view of an embodiment in use according to the present invention.

Refer to FIG. 12 and FIG. 13, a test strip 1 is used together with a test device 2 for sampling and testing. The test device 2 includes a sampling module 21 and a test module 22. The sampling module 21 is located on one side of the test module 22 and is having a blood lancet 23. The test module 22 includes a strip slot 221 that is a half-open slot for receiving the circuit connection part 111 of the test strip 1. One end of the test strip 1 with the circuit connection part 111 is inserted into the strip slot 221 along the direction from the sampling module 21 to the test module 22. An electrical connector 222 is located inside the strip slot 221 and the inserted circuit connection part 111 of the test strip 1 is in contact with the electrical connector 222 of the strip slot 221. Moreover for convenient assembly and disassembly of the test strip 1, a front end of the test strip 1 close to the detection area 10 is extended to form a holding part 107.

The sampling module 21 of the test device 2 consists of a sampling part 211 and a rod part 212. The rod part 212 is used to assembly and disassembly the blood lancet 23. By elasticity, the blood lancet 23 extends from the sampling part 211 automatically and makes punctures at a test area 3 of the patient for collecting the sample 4 (such as blood). A sampling opening 211A is located under the sampling part 211, allowing the blood lancet 23 to pass through. At least one strip positioning part 211D is disposed around the sampling opening 211A and on the bottom of the sampling part 211. The strip positioning part 211D is corresponding to the positioning part 106 of the test strip 1. As shown in the figure, the strip positioning part 211D and the positioning part 106 respectively are a bump and a corresponding hole.

Figure 14:
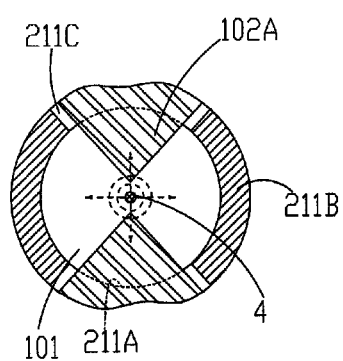
FIG. 14 is a schematic drawing showing a top view of a partial cross section of an embodiment according to the present invention.
Figure 15:
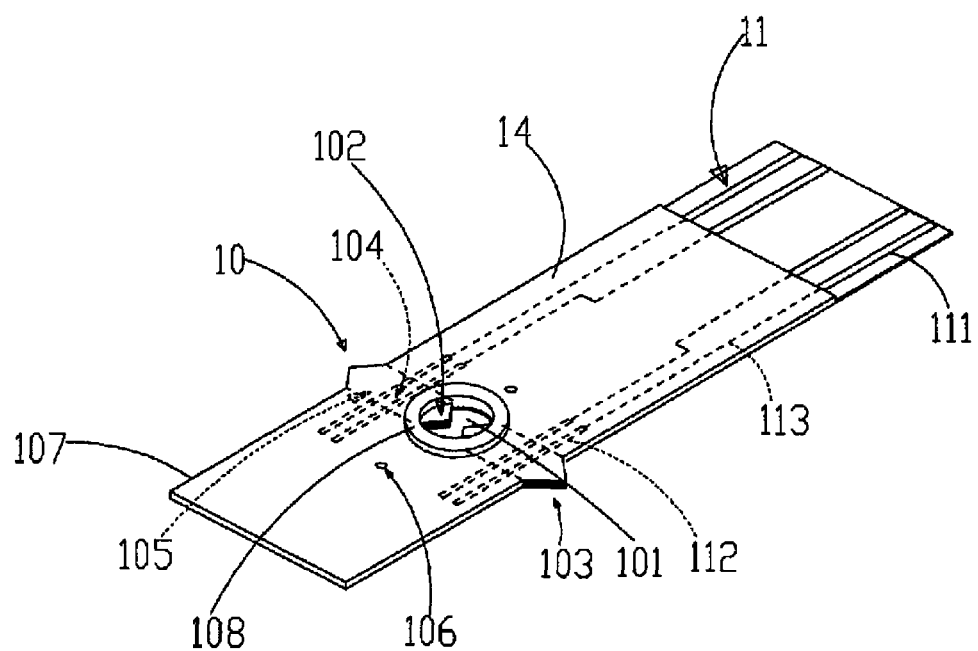
FIG. 15 is a perspective view of another embodiment according to the present invention.
Figure 16:
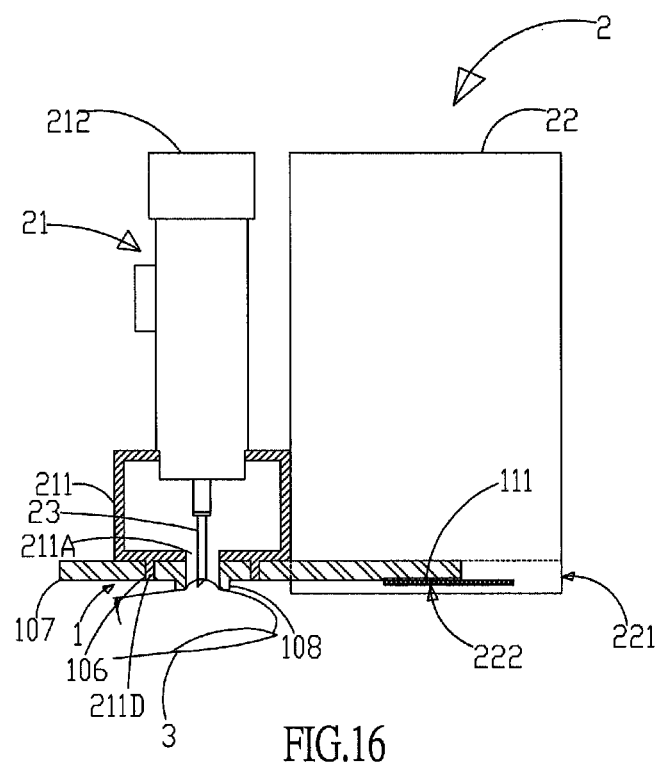
FIG. 16 is a partial cross sectional view of another embodiment in use according to the present invention.
Figure 17:
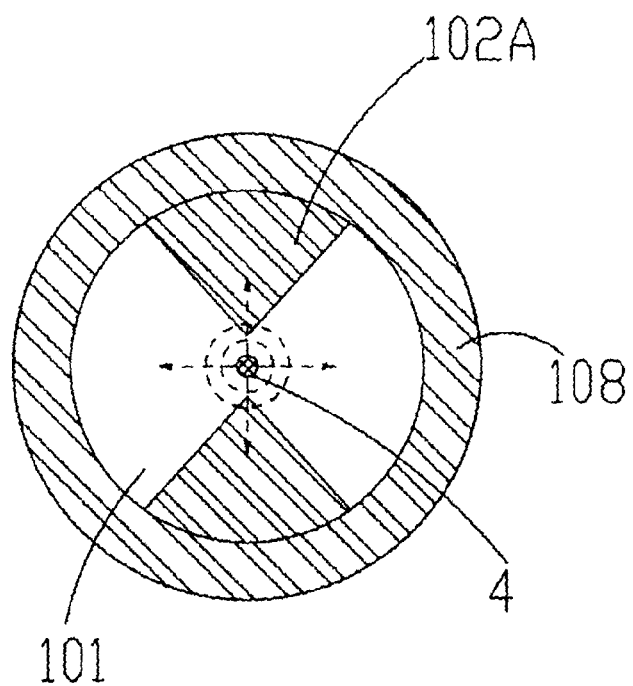
FIG. 17 is a schematic drawing showing a top view of a partial cross section of another embodiment according to the present invention.
Figure 18:
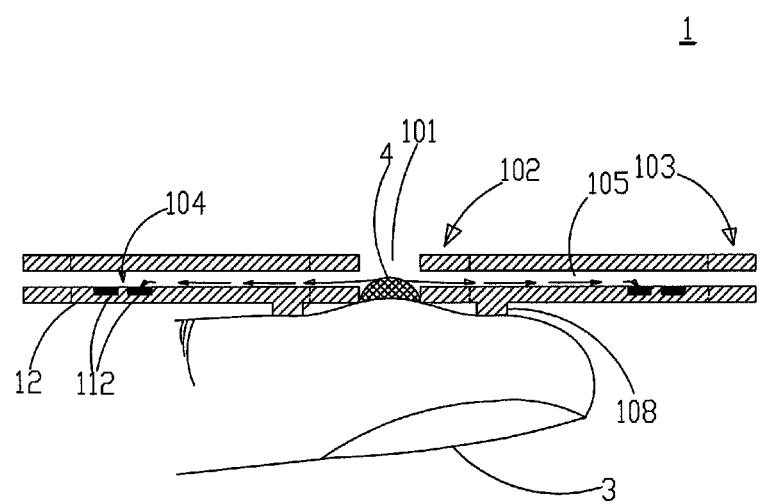
FIG. 18 is a schematic drawing showing a cross section of another embodiment in use according to the present invention.

Refer to FIG. 13 and FIG. 14, a pair of sample pressing parts 211B is disposed on the bottom of the test device 2 (sampling part 211), around the sampling opening 211A. The sample pressing part 211B can be a bar or a curved bar. There are two pressing openings 211C located between the sample pressing parts 211B and beside the inner sampling projections 102A on two sides of the sampling hole 101 of the test strip 1.

After the circuit connection part 111 of the test strip 1 being inserted into the strip slot 221, the detection area 10 of the test strip 1 moves toward the sampling opening 211A of the sampling part 211 so that the strip positioning part 211D is inserted into the positioning part 106 of the test strip 1 for positioning the detection area 10 of the test strip 1 under the test device 2 and allowing the sampling opening 211A to be aligned with the sampling hole 101 of the test strip 1. Thus the blood lancet 23 is passed through the sampling hole 101 to puncture user's fingertip for blood sampling. The holding part 107 on the front end of the test strip 1 is extended out of the front end (or two sides) of the test device 2 for assembly and disassembly of the test strip 1 conveniently. While performing tests, the sample pressing parts 211B project out of the sampling hole 101 and press against the test area 3 of the person to be tested. The test area 3 is pressed so that the speed of the sample 4 flowing out is increased and sufficient sample 4 is provided. Now the sample 4 flows through the two inner sampling openings 102B on two sides of the sampling hole 101 and enters the sampling channels 105. When the sample 4 flows to the two reaction areas 104, the test device 2 applies a voltage to generate a test signal. The test signal is transmitted through the circuit connection part 111 of the test strip 1 to the test module 22. The test module 22 analyzes the test signal so as to get concentration and related data of the sample 4.

Refer from FIG. 15 to FIG. 18, another embodiment is revealed. In the test strip 1, a pressing part 108 is located around the sampling hole 101. The pressing part 108 can be a circular projection or a projection in other shapes. While in use, the pressing part 108 is pressed against the test area 3 of the person to be tested and the blood lancet 23 passes through the sampling hole 101 to puncture the test area 3 and get sufficient sample 4. The pressing part 108 can be disposed around the substrate hole 121, the channel gap 131 (not shown in figure), or the upper cover hole 141. The height of the pressing part 108 ranges from 0.1 mm to 2 mm. In the embodiment shown in FIG. 15, FIG. 16 and FIG. 17, the pressing part 108 is located at the upper cover 14 and is projected from the upper cover 14. In use, the test strip 1 is turned upside down so that the pressing part 108 is pressed against the test area 3. In the FIG. 18, the pressing part 108 is disposed on the substrate and is projected from the substrate 12. The pressing part 108 is also used to press against the test area 3.

In summary, the test strip of the present invention used for tests is based on electrochemical techniques. The sampling hole of the test strip is arranged with sampling openings for collecting samples. The sampling opening draws and guides the sample into the reaction area and electrochemical reactions occur at that area. The test strip further includes a pressing part disposed around the sampling hole. The pressing part is used to against a test area of a person to be tested. Thus the sample flows faster from the test area to the reaction area and electrochemical reactions occur. The present invention further provides a test device used in combination with the test strip. The test device provides both sampling and testing functions. Due to simple structure, the cost of the test device is reduced. Moreover, the test strip disposed with the pressing part can prevent cross-infection.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A test strip comprising:
    a detection area having:
        a sampling hole;
        at least one sampling channel corresponding to the sampling hole;
        at least one reaction area located in the sampling channel; and
        at least one pressing part located around the sampling hole;
    a circuit system electrically connected to the reaction area;
    a substrate having a substrate hole;
    a spacer layer disposed over the substrate, the spacer layer having a channel gap corresponding to the substrate hole;
    an upper cover disposed over the spacer layer and having an upper cover hole; and
    at least one inner sampling projection located between the sampling hole and the sampling channel, the inner sampling projection extending and projecting from an edge of the sampling channel to the sampling hole, the inner sampling projection comprising a substrate inner projection of the substrate and an upper-cover inner projection of the upper cover and the edge of the inner sampling projection having an inner sampling opening in communication with the sampling hole and the sampling channel;
    wherein an overlapped area of the substrate hole, the channel gap and the upper cover hole is defined as the sampling hole, the sampling channel is formed among the channel gap, the substrate and the upper cover.

2. The test strip as claimed in claim 1, wherein the pressing part is disposed around the substrate hole, the channel gap or the upper cover hole.

3. The test strip as claimed in claim 1, wherein a diameter of the sampling hole ranges from 0.4 mm to 4 mm.

4. The test strip as claimed in claim 1, wherein a height of the pressing part ranges from 0.1 mm to 2 mm.

5. The test strip as claimed in claim 1, wherein a distance between a front end of the inner sampling projection and the center of the sampling hole ranges from 0.2 mm to 2 mm.

6. The test strip as claimed in claim 1, further including:
    at least one positioning part defined as an insertion hole, a notch or a bump.

7. The test strip as claimed in claim 1, further including:
    at least one outer sampling area located on an outer side of the test strip and communicated with the sampling channel.

8. A test strip comprising:
    a detection area having:
        a sampling hole;
        at least one sampling channel corresponding to the sampling hole;
        at least one reaction area located in the sampling channel; and
        an inner sampling area disposed around the sampling hole and having an inner sampling opening on one edge thereof, the inner sampling opening communicated with the sampling hole and the sampling channel;
    at least one outer sampling area located on an outer side of the test strip and having an outer sampling opening in communication with the sampling channel;
    a circuit system electrically connected to the reaction area;
    a substrate having a substrate hole;
    a spacer layer disposed over the substrate and having a channel gap corresponding to the substrate hole; and
    an upper cover disposed over the spacer layer and having an upper cover hole;
    wherein an overlapped area of the substrate hole, the channel gap and the upper cover hole is defined as the sampling hole, the sampling channel is formed among the channel gap, the substrate and the upper cover;
    the inner sampling area further includes:
        at least one inner sampling projection located between the sampling hole and the sampling channel, the inner sampling projection extending and projecting from an edge of the sampling channel to the sampling hole, the inner sampling projection comprising a substrate inner projection of the substrate and an upper-cover inner projection of the upper cover and the inner sampling opening located at the edge of the inner sampling projection in communication with the sampling hole and the sampling channel.

9. The test strip as claimed in claim 8, wherein a distance between a front end of the inner sampling projection and the center of the sampling hole ranges from 0.2 mm to 2 mm.

10. The test strip as claimed in claim 8, wherein the upper cover hole and the substrate hole are different diameters, the inner sampling area is formed between the upper cover hole and the substrate hole.

11. The test strip as claimed in claim 8, wherein a diameter of the sampling hole ranges from 0.4 mm to 4 mm.

12. The test strip as claimed in claim 8, further including: at least one pressing part disposed around the sampling hole.

13. The test strip as claimed in claim 8, further including: at least one positioning part defined as an insertion hole, a notch or a bump.

14. The test strip as claimed in claim 8, wherein the outer sampling area further includes: an outer sampling projection that is mounted with the outer sampling opening.

\* \* \* \* \*